United States Patent
Ko et al.

(10) Patent No.: US 11,452,558 B2
(45) Date of Patent: Sep. 27, 2022

(54) RF TREATMENT APPARATUS, METHOD OF CONTROLLING RF TREATMENT APPARATUS AND SKIN TREATMENT METHOD USING RF ENERGY

(71) Applicant: LUTRONIC CORPORATION, Goyang (KR)

(72) Inventors: Kwang Chon Ko, Paju (KR); Richard Howard Cohen, San Rafael, CA (US)

(73) Assignee: LUTRONIC CORPORATION, Goyang (KR)

( * ) Notice: Subject to any disclaimer, the term of this patent is extended or adjusted under 35 U.S.C. 154(b) by 871 days.

(21) Appl. No.: 16/070,514

(22) PCT Filed: Feb. 28, 2018

(86) PCT No.: PCT/KR2018/002438
§ 371 (c)(1),
(2) Date: Jul. 16, 2018

(87) PCT Pub. No.: WO2018/182188
PCT Pub. Date: Oct. 4, 2018

(65) Prior Publication Data
US 2021/0204996 A1    Jul. 8, 2021

(30) Foreign Application Priority Data
Mar. 31, 2017  (KR) .................. 10-2017-0041802

(51) Int. Cl.
*A61B 18/12*   (2006.01)
*A61B 18/14*   (2006.01)
*A61B 18/00*   (2006.01)

(52) U.S. Cl.
CPC .......... *A61B 18/1206* (2013.01); *A61B 18/14* (2013.01); *A61B 2018/00452* (2013.01);
(Continued)

(58) Field of Classification Search
CPC ................ A61B 18/14; A61B 18/1206; A61B 2018/00702; A61B 2018/00779;
(Continued)

(56) References Cited

U.S. PATENT DOCUMENTS 6,413,255 B1 *   7/2002   Stern ...................... A61B 18/14
                                                  606/41
6,430,446 B1 *   8/2002   Knowlton ........... G06F 16/9017
                                                  607/101
(Continued)

FOREIGN PATENT DOCUMENTS

JP    5412602 B2    11/2013
JP    5732507 B2     6/2015
(Continued)

OTHER PUBLICATIONS

International Search Report for International Patent Application No. PCT/KR2018/002438, dated Jun. 27, 2018.

*Primary Examiner* — Michael F Peffley

(57) ABSTRACT

The present invention relates to an RF treatment apparatus controlling the RF energy so that the target tissue is maintained within a range of a treatment temperature if the target tissue is determined to have reached the treatment temperature based on the impedance, a method of controlling the RF treatment apparatus, and a skin treatment method using RF energy. The RF treatment apparatus, the method of controlling the RF treatment apparatus and the skin treatment method using RF energy according to the present invention have an effect in that they can improve the accuracy and efficiency of treatment because whether a target tissue corresponds to a treatment temperature is determined based on impedance of the tissue and the volume of the target tissue corresponding to the treatment temperature can be
(Continued)

maximized while maintaining the target tissue to the treatment temperature for a predetermined time.

21 Claims, 21 Drawing Sheets

(52) U.S. Cl.
CPC .............. *A61B 2018/00589* (2013.01); *A61B 2018/00672* (2013.01); *A61B 2018/00678* (2013.01); *A61B 2018/00702* (2013.01); *A61B 2018/00714* (2013.01); *A61B 2018/00761* (2013.01); *A61B 2018/00767* (2013.01); *A61B 2018/00875* (2013.01)

(58) Field of Classification Search
CPC ........... A61B 2018/00875; A61B 2018/00464; A61B 2018/00452; A61B 2018/00458; A61B 2018/0047; A61B 2018/00577; A61B 2018/00708; A61B 2018/0072; A61B 2018/00755; A61B 2018/00767; A61B 2018/00827; A61B 2018/00833
See application file for complete search history.

(56) References Cited

U.S. PATENT DOCUMENTS

| | | | | |
|---|---|---|---|---|
| 7,137,980 | B2* | 11/2006 | Buysse | A61B 18/1206 606/34 |
| 9,108,052 | B2* | 8/2015 | Jarrard | A61B 18/14 |
| 2002/0091385 | A1* | 7/2002 | Paton | A61B 18/1442 606/51 |
| 2012/0150168 | A1* | 6/2012 | Adanny | A61N 1/0476 606/33 |
| 2013/0338740 | A1 | 12/2013 | Honda et al. | |
| 2014/0025062 | A1* | 1/2014 | Rosenberg | A61B 18/18 606/33 |
| 2018/0133469 | A1* | 5/2018 | Palero | A61N 1/328 |

FOREIGN PATENT DOCUMENTS

| | | | | |
|---|---|---|---|---|
| KR | 10-2012-0090007 A | 8/2012 | | |
| KR | 10-1547299 B1 | 8/2015 | | |
| KR | 10-1633707 B1 | 6/2016 | | |
| WO | 2009015278 A1 | 1/2009 | | |
| WO | 2010098784 A1 | 9/2010 | | |
| WO | WO 2016/162234 | * 10/2016 | ............... A61N 1/32 |
| WO | WO2017018205 A1 | 2/2017 | | |

* cited by examiner

RF TREATMENT APPARATUS, METHOD OF CONTROLLING RF TREATMENT APPARATUS AND SKIN TREATMENT METHOD USING RF ENERGY

CROSS-REFERENCE TO RELATED APPLICATION

The present specification is a U.S. National Stage of International Patent Application No. PCT/KR2018/002438 filed Feb. 28, 2018, which claims priority to and the benefit of Korean Patent Application Nos. 10-2017-0041802 filed in the Korean Intellectual Property Office on Mar. 31, 2017, the entire contents of which are incorporated herein by reference.

TECHNICAL FIELD

The present invention relates to an RF treatment apparatus, a method of controlling the RF treatment apparatus, and a skin treatment method using RF energy and, more particularly, to an RF treatment apparatus controlling RF energy using calculated impedance, a method of controlling the RF treatment apparatus, and a skin treatment method using RF energy.

BACKGROUND ART

A method of treating a tissue may be divided into a method of treating a tissue outside the tissue and an invasive treatment method of treating a tissue by inserting some of or the entire treatment apparatus into the tissue. The invasive treatment method basically uses a treatment apparatus having a thin-necked insertion unit, such as a needle or a catheter. Treatment is performed after the treatment apparatus is inserted into a target location within a tissue.

The invasive treatment method includes various treatment behaviors, such as delivering a treating substance to the inside of a tissue, performing surgical treatment through a mechanical operation in the state in which a predetermined tissue within a tissue is adjacent, or delivering energy to a target location within a tissue. The treatment method has been disclosed in Korean Patent Application Publication No. 10-2011-0000790, and is applied in various methods.

However, the existing RF treatment apparatus has a problem in that a tissue may be damaged because excessive energy is applied when applying high energy within a short time.

DISCLOSURE

Technical Problem

The present invention has been made to solve the aforementioned problem of the conventional RF treatment apparatus, and an object of the present invention is to provide an RF treatment apparatus capable of controlling RF energy so that the period during which a tissue is maintained to a treatment temperature can be extended. A temperature of the tissue is estimated and RF energy is controlled based on a parameter into which an impedance value has been incorporated. Accordingly, the tissue does not rise up to a temperature at which ablation occurs and is maintained to a temperature at which coagulation occurs, so the region in which coagulation occurs is increased.

Technical Solution

As means for solving the object, there may be provided an RF treatment apparatus, including an RF generator generating RF energy, an electrode applying the RF energy to a target tissue, a sensor unit configured to sense the RF energy, and a controller controlling output of the RF generator, receiving a sensing value from the sensor unit, calculating impedance of the tissue, and controlling the RF energy so that the target tissue is maintained within a range of a treatment temperature if the target tissue is determined to have reached the treatment temperature based on the impedance.

In this case, the controller may determine the target tissue is determined to have reached the treatment temperature if the impedance of the tissue to have reached within a predetermined range.

Furthermore, the controller may determine the target tissue is determined to have reached the treatment temperature if a change in the impedance of the tissue to have reached within a predetermined range.

Furthermore, the controller may determine whether the target tissue has reached the treatment temperature if a change in the impedance from a current to a predetermined time before has reached within a preset range.

Meanwhile, the controller may calculate an cumulative change in the impedance of the tissue from a current to a predetermined time before so that the impedance of the tissue is maintained within a predetermined range, and may control the RF energy so that the cumulative change has reached within a preset range.

Furthermore, when controlling the RF energy, the controller may control the RF energy by increasing RF power of the RF energy when the impedance is less than a threshold and decreasing the RF power of the RF energy when the impedance is the threshold or more.

Furthermore, the controller may perform the control for a predetermined control time.

Moreover, the controller may control a voltage when controlling the RF energy.

In this case, the controller may apply the RF energy while maintaining constant RF power during a first application time from a start of treatment, may determine whether the target tissue has reached the treatment temperature after a lapse of the first application time, and may control the RF power when the target tissue reaches the treatment temperature.

Furthermore, the electrode may have at least one of a contact type and an insertion type.

In addition, there may be provided a method of controlling an RF treatment apparatus, including the steps of positioning an electrode in a target tissue, applying RF energy, calculating impedance of the target tissue by sensing the RF energy and determining whether the target tissue has reached a treatment temperature, and controlling the RF energy so that the impedance of the target tissue is maintained within a predetermined range for a predetermined time if the target tissue is determined to have reached the treatment temperature.

In this case, the step of determining whether the target tissue has reached the treatment temperature may include determining the target tissue to have reached the treatment temperature if a change in the impedance of the target tissue corresponds to a predetermined range.

Furthermore, the step of determining whether the target tissue has reached the treatment temperature may be performed after the RF energy is applied for a first application time in the step of applying the RF energy.

Meanwhile, the step of controlling the RF energy may be performed by increasing RF power of the RF energy when the impedance is less than a threshold. Furthermore, the step of controlling the RF energy may be performed by decreasing RF power of the RF energy when the impedance is a threshold or more.

Moreover, the step of controlling the RF energy may include controlling power of the RF energy so that an absolute value of the change in the impedance is maintained within the predetermined range.

Furthermore, the step of controlling the RF energy may be performed by controlling a voltage of the RF energy.

Meanwhile, the step of controlling the RF energy may be performed for a preset third application time so that a volume belonging to the target tissue and corresponding to the treatment temperature is increased.

Furthermore, the step of controlling the RF energy may be configured so that initial power of the RF energy is decreased.

Meanwhile, the step of positioning the electrode in the target tissue may be performed using at least one of a contact and insertion of the electrode on and into the target tissue.

In addition, there may be provided a skin treatment method using RF energy, including the steps of positioning an electrode in a tissue, heating the tissue to a treatment temperature by applying RF energy to the electrode, measuring the RF energy applied to the tissue, calculating impedance of the tissue to which the RF energy is applied, comparing a parameter into which the impedance from the current time to the predetermined time with a predetermined range, and maintaining the tissue to a predetermined treatment temperature for a predetermined time by controlling power of the RF energy based on a result of the comparison of the parameter and the predetermined range so that a coagulation occurrence area is expanded.

In this case, the step of controlling the RF energy based on a result of the comparison may include increasing the power of the RF energy when the parameter is less than a threshold and decreasing the power of the RF energy when the parameter is the threshold or more.

Meanwhile, the parameter may be defined as any one of a mean of impedance values measured for a time interval from a current time to a predetermined time, a product of impedance values, a change in an impedance value, a change in a mean of impedance values, and an absolute value of an impedance change.

Advantageous Effects

The RF treatment apparatus, the method of controlling the RF treatment apparatus, and the skin treatment method using RF energy according to the present invention have effects in that they can prevent damage to a tissue by determining the ablation of the tissue to be imminent and cutting off RF energy prior to the imminent ablation and they are capable of an efficient operation by delivering RF energy of proper power based on the state of a tissue.

MODE FOR INVENTION

Figure 1:
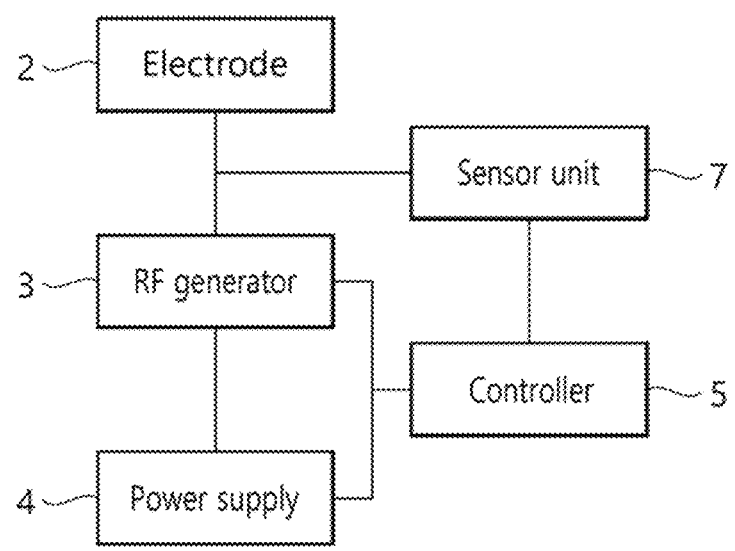
FIG. 1 is a conceptual diagram of an RF treatment apparatus according to the present invention.

Hereinafter, an RF treatment apparatus, a method of controlling the RF treatment apparatus, and a skin treatment method using RF energy according to embodiments of the present invention are described in detail with reference to the accompanying drawings. Furthermore, in the following description of the embodiments, elements may be named differently in the field to which the present invention pertains. However, if the elements have functional similarity and identity, they may be considered to be equivalent elements although they adopt modified embodiments. Furthermore, reference numerals assigned to respective elements are written for convenience of description. However, contents shown in the drawings in which the reference numerals are written do not restrict respective elements to the ranges in the drawings. Likewise, although the elements in the drawings adopt partially modified embodiments, they may be considered to be equivalent elements if the elements have functional similarity and identity. Furthermore, a description of an element is omitted if the element is recognized as being an element that must be naturally included in view of the level of a person having ordinary skill in the art.

Hereinafter, a "treatment apparatus" includes all apparatuses for treating mammals including people. The treatment apparatus may include may include various treatment apparatuses used to improve a lesion or the state of a tissue. For example, the treatment apparatus includes an apparatus transferring treating substances, such as medicines, anesthetic, and stem cells, an operation apparatus for surgically treating a predetermined tissue, and various treatment apparatuses applying RF energy.

Hereinafter, a "tissue" means a set of cells forming various body organs of an animal including people, and includes various tissues forming various organs within the body, including a skin tissue.

FIG. 1 is a conceptual diagram of an RF treatment apparatus according to the present invention. The RF treatment apparatus is configured to treat a tissue by applying RF energy to the inside of the tissue to denaturize the tissue. As shown, the RF treatment apparatus according to the present invention may include an electrode 2, an RF generator 3, a power supply 4, a sensor unit 7, a controller 5 and a reference unit.

The electrode 2 is configured to apply RF energy from the RF treatment apparatus to the skin. A plurality of electrodes 2 may be configured to apply energy to a plurality of points. The electrode 2 has a bipolar type, and may be configured so that RF energy is concentrated on a lesion portion positioned between each of pairs of the electrodes 2. Furthermore, a plurality of pairs of electrodes 2 is provided, and may be configured to generate fractional damage within a tissue. The plurality of electrodes 2 may be configured in an insertion and/or contact type. If the electrodes are configured in the insertion type, a plurality of micro needles may be configured to be inserted into a skin tissue and to generate heat in a deep part. Furthermore, if the electrodes are configured in the contact type, they may come into contact with the skin and generate deep part heat. In this case, an insulating part may be applied to each electrode 2 so that an RF energy transmission condition is changed. In this case, the configuration of the electrode 2 may be modified and applied in various manners, and thus a further detailed description thereof is omitted.

The RF generator 3 is configured to be supplied with power from the power supply 4 and to generate RF energy. The RF generator 3 generates RF energy used for treatment through the electrode 2. In this case, the RF generator 3 is configured to change the frequency, voltage, etc. of the RF energy, if necessary.

The sensor unit 7 is configured to measure an output value of RF energy. The sensor unit 7 may be provided on an electrical path between the electrodes 2 from the RF generator 3, and is configured to measure current, a voltage and power applied to the electrodes 2. An impedance value of a tissue can be calculated based on the current, a voltage and power.

The controller 5 is configured to receive a sensing value from the sensor unit 7 and to control the RF generator 3. Furthermore, the controller 5 is configured to control the RF generator 3 and other elements when operating in various modes in response to a user input. The controller 5 may function to determine the state within a tissue while RF energy is applied and to control the applied RF energy or block the RF energy based on the state of the tissue. In this case, the controller 5 may determine the state within the tissue or output of the RF energy based on data stored in the reference unit. Meanwhile, although the reference unit is not provided, the controller 5 may perform control using a predetermined setting value.

Hereinafter, RF energy applied to the inside of a tissue, a temperature of the tissue, and a change in the state of the tissue are described with reference to FIG. 2.

Figure 2:
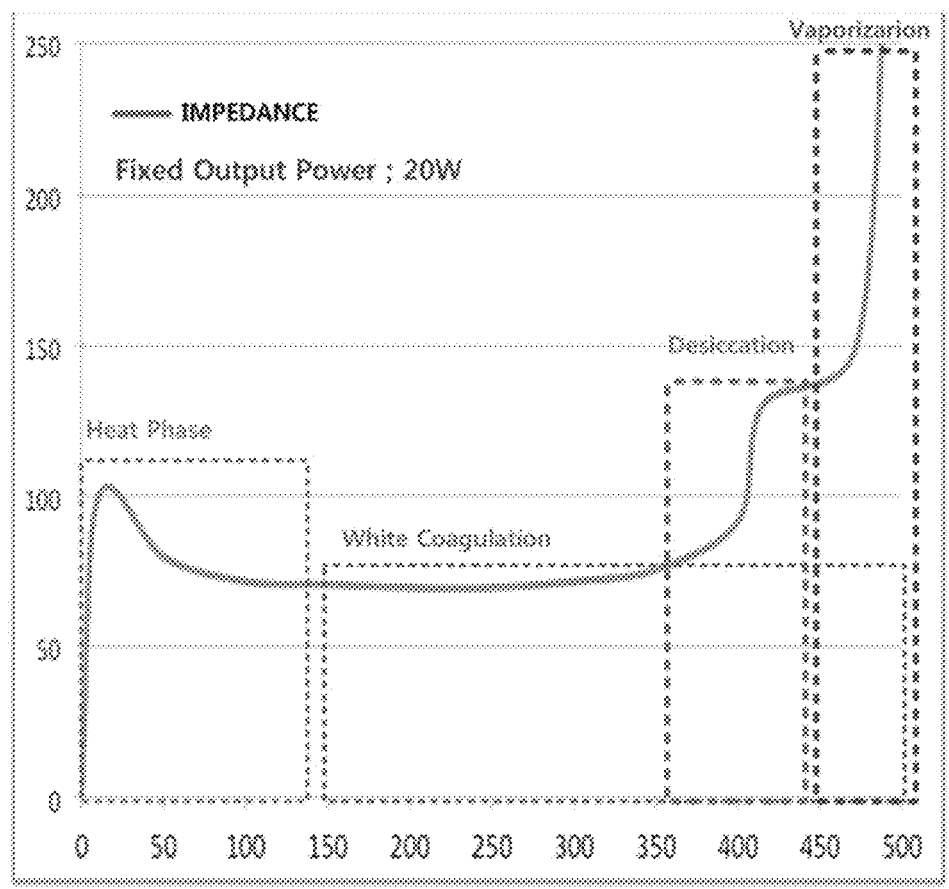
FIG. 2 is a diagram showing an impedance change according to a temperature rise of a tissue.

FIG. 2 is a diagram showing an impedance change according to a temperature rise of a tissue. When RF energy is applied, a tissue is denaturized. Such denaturalization may be divided into a heat phase, a coagulation occurrence phase, a desiccation occurrence phase and a vaporization occurrence phase. The heat phase corresponds to the section in which a tissue rises up to a treatment temperature as RF energy is applied. In this case, when the temperature of the tissue reaches about 44° C., tissue necrosis begins. Thereafter, when the temperature of the tissue reaches about 70° C., coagulation of the tissue starts. Thereafter, when the temperature of the tissue reaches about 90° C., desiccation occurs. In this case, cells lose moisture, but the ultrastructure of the tissue may remain intact. Thereafter, when the temperature of the tissue reaches 100° C., moisture starts to be vaporized. When the tissue is further heated, carbonization occurs about 200° C.

Impedance of the tissue at this time is described. When RF energy of the same power is applied, the tissue is denaturized and an impedance value is greatly changed depending on a temperature rise of the tissue. That is, in the heat phase, after a sudden rise of the impedance, a stabilization phase in which a change (AZ) in the impedance is reduced appears. This corresponds to the coagulation occurrence phase. Thereafter, a phase in which a sudden rise of the impedance occurs corresponds to the desiccation occurrence phase. In contrast, the current state of a tissue may be estimated by measuring impedance of the tissue and checking a variation tendency. Predeterminedally, it may be seen that after the RF energy is applied, if an impedance value is stabilized within a predetermined range after a lapse of a predetermined time, temperature of the tissue is about 70° C. and coagulation occurs. Thereafter, it may be seen that when a sudden rise of the impedance occurs, the impedance becomes the desiccation occurrence phase in which ablation occurs.

In other words, an important factor in the aspect of control of a temperature of a tissue and energy based on the temperature is impedance of the tissue. The impedance of the tissue tends to be generally similar according to a temperature change (as a treatment time elapses). An increment phase and a sudden increment phase appear after the phase in which impedance of a tissue is gradually decreased.

The controller performs control based on a calculated impedance value so that RF energy is optimized and applied depending on treatment purposes. For example, the controller may perform control so that a local portion is denaturized until right before ablation for the purposes of removal of a scar, removal of a tissue, etc., or coagulation occurs in a wide volume for the retightening of the skin.

Hereinafter, two treatment modes of the functions of the controller are described. An ablation prevention mode is described with reference to FIGS. 4 to 7, and a coagulation mode is described with reference to FIGS. 8 to 12. In this case, each mode may be optionally applied by a user.

I. Ablation Prevention Mode

Figure 3A:
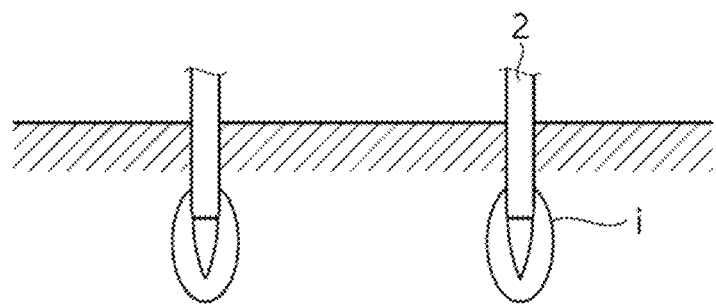
FIGS. 3a and 3b are conceptual diagrams when ablation within a tissue occurs.
Figure 3B:
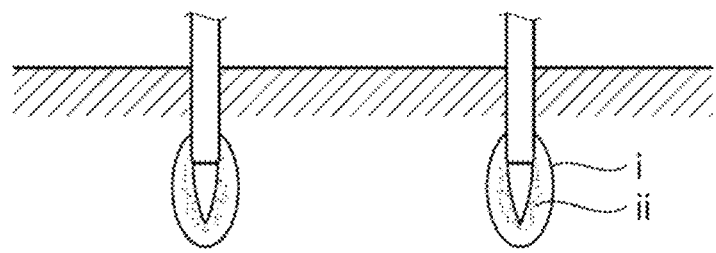
Figure 4A:
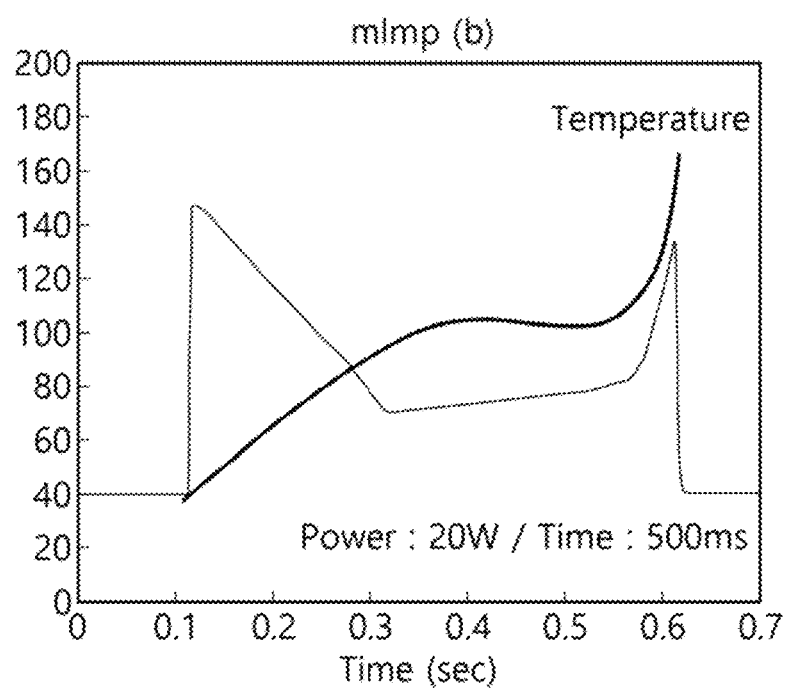
FIGS. 4a and 4b are impedance and temperature graphs of a tissue when ablation occurs.
Figure 4B:
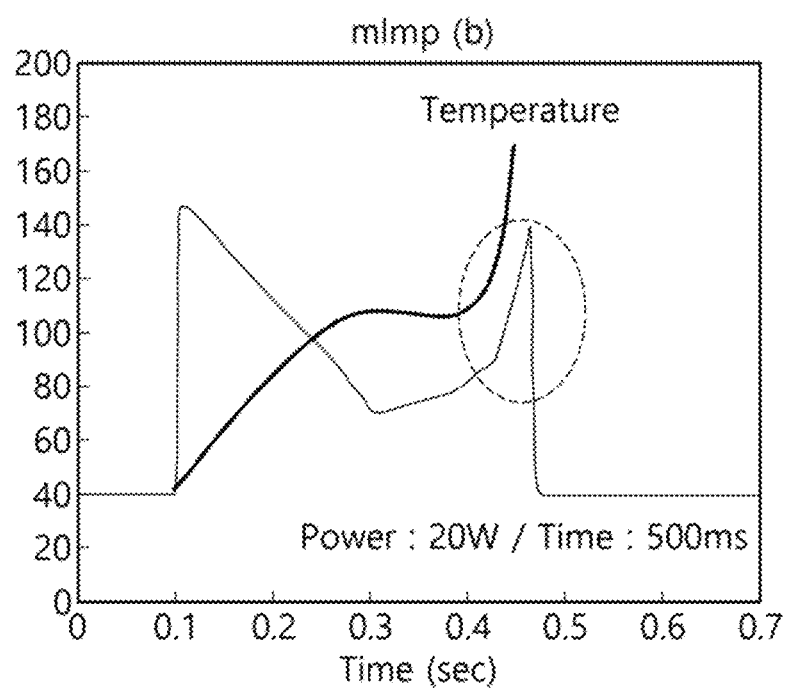
Figure 5A:
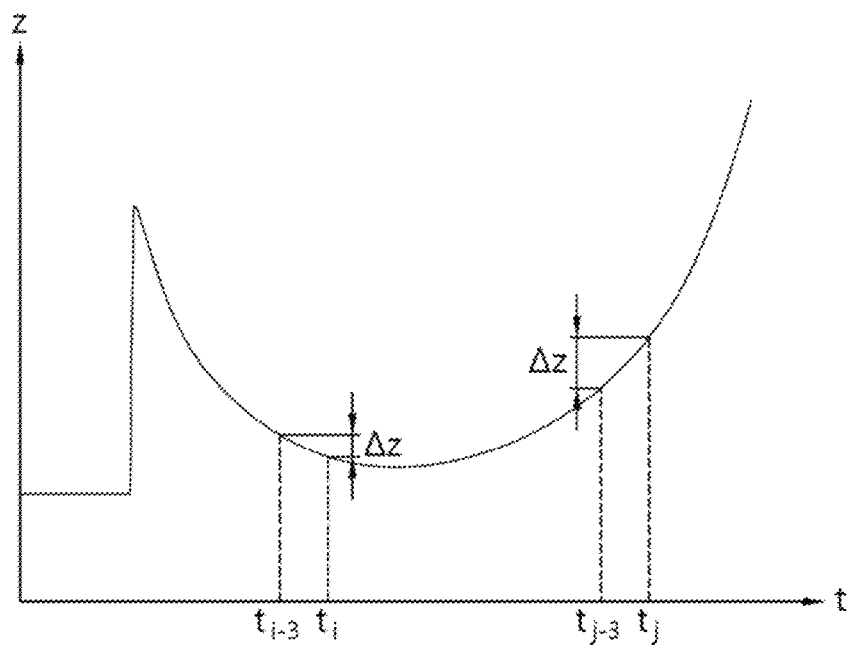
FIGS. 5a and 5b are graphs of impedance in the ablation prevention mode.
Figure 5B:
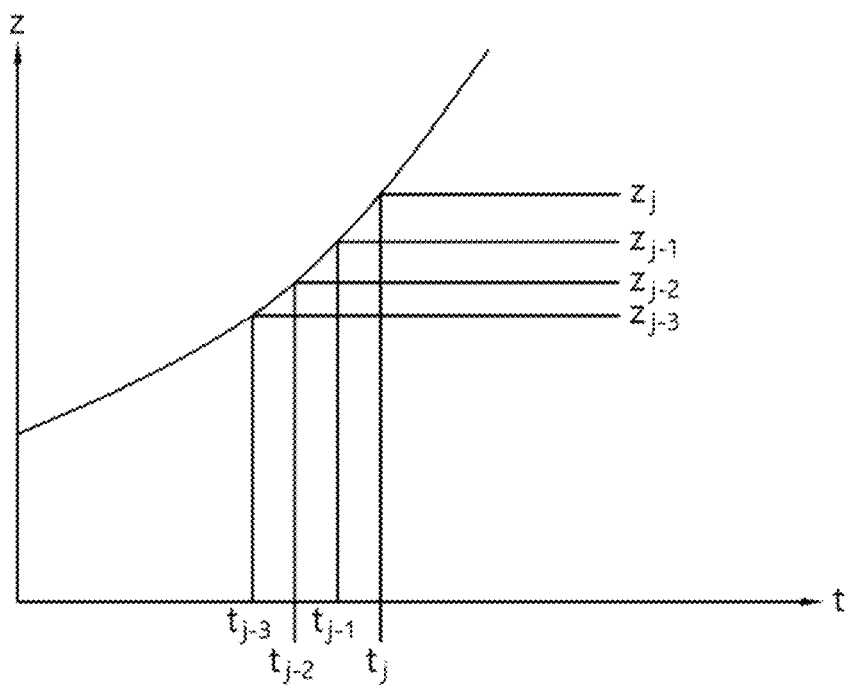
Figure 6:
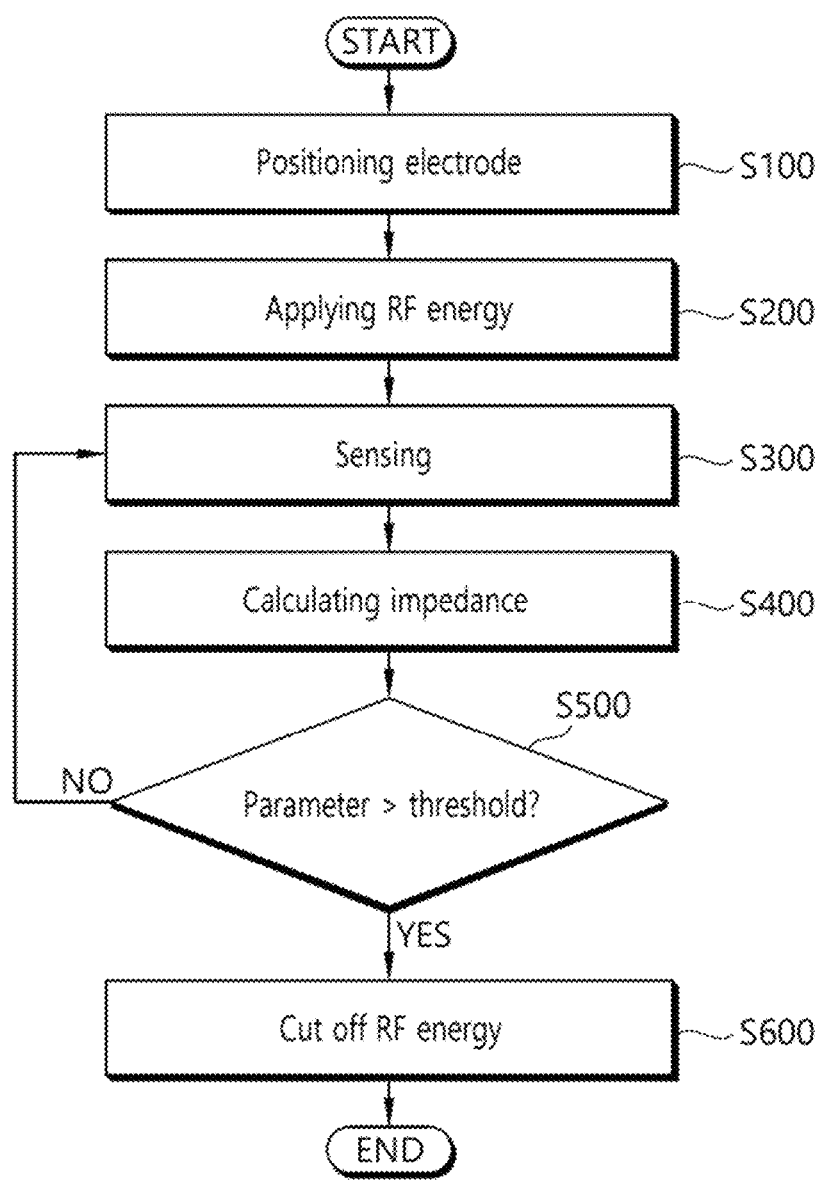
FIG. 6 is a flowchart of a method of controlling an RF treatment apparatus in the ablation prevention mode.
Figure 7A:
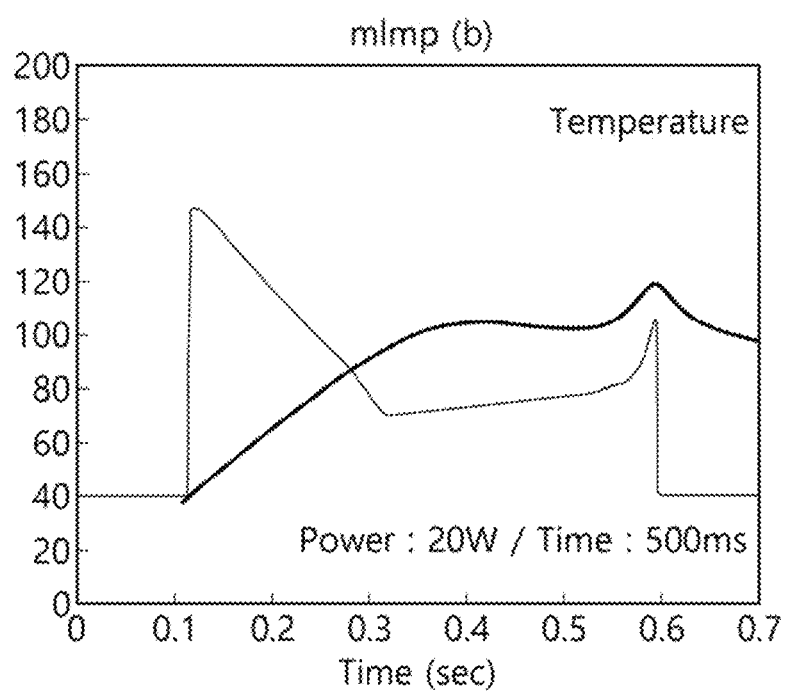
FIGS. 7a and 7b are impedance and temperature graphs of a tissue when the ablation prevention mode is performed.
Figure 7B:
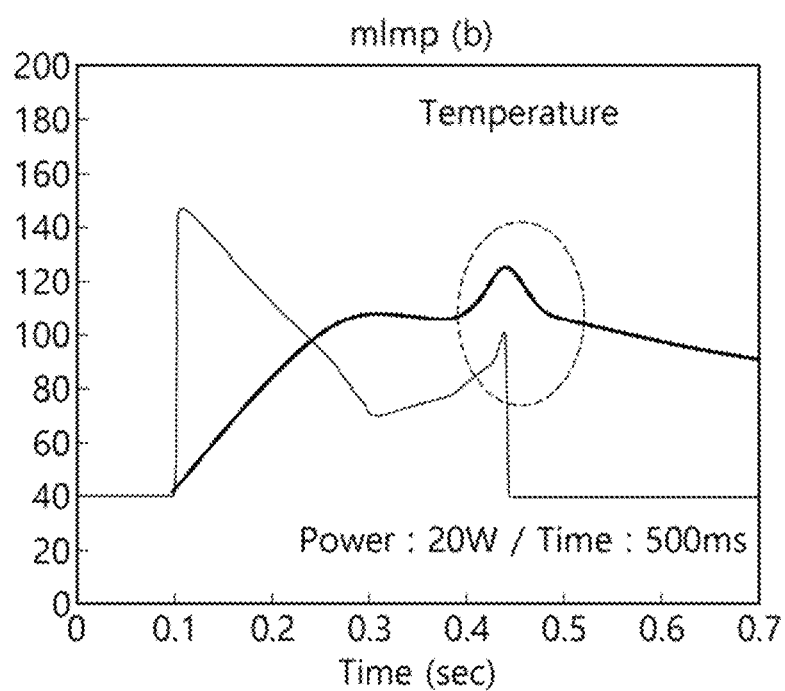

FIGS. 3a and 3b are conceptual diagrams when ablation within a tissue occurs. FIGS. 4a and 4b are impedance and temperature graphs of a tissue when ablation occurs. FIGS. 5a and 5b are graphs of impedance in the ablation prevention mode. FIG. 6 is a flowchart of a method of controlling an RF treatment apparatus in the ablation prevention mode. FIGS. 7a and 7b are impedance and temperature graphs of a tissue when the ablation prevention mode is performed.

Referring to FIG. 3a, there are shown a region denaturized because coagulation has occurred in a tissue (i) and a region in which ablation has occurred (ii) thereafter. This corresponds to a case where the ablation region is expanded because a temperature of a tissue around the electrode rises rapidly compared to the speed at which the region where coagulation has occurred is expanded. Accordingly, the ablation prevention mode is applied to prevent ablation in the tissue and to denaturize a proper region.

Referring to FIGS. 4a and 4b, there are shown temperatures and impedance when RF energy is applied to different persons. As shown, although the RF energy is applied with the same power for the same application time, points of time at which the temperature rises suddenly are different in the persons. Accordingly, if the RF energy is not controlled, unwanted damages may occur. For example, if RF energy having power of 20 W is applied for 0.5 second, unlike in FIG. 4a, ablation occurs in the case of FIG. 4b and thus damage to a tissue occurs. Accordingly, the controller blocks power in a step prior to the occurrence of ablation at a predetermined point of time in order to prevent such damage.

The function of the controller 5 is described below based on a sampling time T. The controller 5 controls the RF generator 3 so that power of RF energy is controlled or the RF energy is blocked. Power control of the RF generator 3 is first described below.

To constantly maintain power of RF energy applied to a tissue during treatment is preferred in terms of the prevention of damage to the tissue attributable to the sudden application of energy, the treatment range of the tissue, and accuracy of a treatment effect. In this case, if a method of measuring a temperature within the tissue is used, time delay occurs due to the temperature measurement, and thus control of the output of the RF energy is not properly incorporated. Accordingly, it is preferred to measure and incorporate impedance of the tissue, but a fine change in the volume occurs if fractional damage occurs. Furthermore, since treatment is performed within a short time, an impedance value, that is, an electrical characteristic of the tissue, may be sensitively changed. Accordingly, temperature measurement is used for control through a predetermined step.

Accordingly, an impedance effective value (i.e., root-mean-square (RMS)) of a tissue may be obtained based on values obtained by measuring a voltage, current and power continuously (at T intervals) using the sensor unit 7 while RF energy is applied.

Detailed contents are described below.

At a point of time T that is an initial step 1, an R1 value may be derived as the RMS of a voltage V1, current I1 and power P1.

Thereafter, at a point of time 2T that is step 2, R2 may be derived as the RMS of a voltage V2, current I2 and power P2.

In this case, referring to a power relation in step 1 and step 2, a power loss occurs due to a change in the reactance. At this time, a power factor may be defined as follows.

$$\varphi = PRMS(t)/PRMS(t-1)$$

In this case, the power factor becomes a reactance value in step 2. Accordingly, the reactance value in step 2 can be obtained although the impedance value of the tissue is not measured.

An example of detailed numerical values is shown in Table 1.

TABLE 1

| STEP | 1 | 2 | 3 | 4 |
|---|---|---|---|---|
| V [V] | 1 | 1 | 1 | 1 |
| I [A] | 1 | 2 | 2 | 1 |
| P [W] | 1 | 2 | 2 | 1 |
| Power factor | — | 2 | 1 | 1.5 |
| Resistance [Ω] | 1 | 0.5 | 0.5 | 1 |
| Reactance | — | 2 | 1 | 1.5 |

As described above, the impedance value of the tissue is calculated in each step. Power suitable for a corresponding tissue based on an impedance value is determined by matching the impedance value with data stored in the reference unit 6. Thereafter, the tissue can be properly treated within a short time by controlling an output voltage of the RF generator 3 so that RF energy of a determined power value is applied.

The cutting off of RF energy, that is, a function of the controller 5, is described below.

The controller 5 may be configured to block applied RF energy if it determines that impedance has suddenly increased for a predetermined period. This is for preventing ablation occurring due to a sudden rise of a tissue temperature.

The controller 5 may determine that impedance has increased for a predetermined period based on a parameter value defined as the product of a rising time "Trising", that is, a predetermined period during which impedance has increased, and the mean (Zvalue) of impedance corresponding to the rising time "Trising" as follows.

Parameter=Trising×Zvalue

A determination of whether impedance has increased for a predetermined period is described based on a sampling period T. Whether impedance has increased is determined for a time interval from the present point of time to a predetermined time. In this case, if the rising time, that is, the time from the current time to the predetermined time, is too large, rapid handling is difficult. If the rising time is too small, it may be sensitive to low noise. Accordingly, it is preferred to properly determine the rising time.

FIGS. 5a and 5b are graphs of impedance in the ablation prevention mode. As shown, whether a parameter exceeds a first threshold is determined every step after a predetermined time. A case where a predetermined time interval is three sampling time intervals is described as an example with reference to FIG. 5a. In the case of ti at present, an impedance value calculated during a time interval until ti-3, ti-2, ti-1, and ti may be applied to a parameter value. Meanwhile, impedance is reduced at ti. At this time, energy is not blocked. Predeterminedally, referring to FIG. 5b showing an enlarged rising phase, in the case of tj, during time up to tj-3, tj-2, tj-1, and tj, impedance rise up to Zj-3, Zj-2, Zj-1, and Zj. At this time, a change (ΔZ) in the impedance continues to rise. This corresponds to a case where the parameter value exceeds the first threshold or becomes the first threshold or more. Accordingly, the RF energy may be blocked. When the RF energy will be blocked at any point of time during the period in which the impedance rises may be different according to circumstances. Predeterminedally, a location is different depending on a set first threshold. If a high first threshold is set, the RF energy may be blocked at a higher temperature. If a low first threshold is set, the RF energy may be blocked at a low temperature.

That is, the controller blocks RF energy if the following condition is satisfied.

Parameter>first threshold

Furthermore, impedance may be determined to have increased for a predetermined period if any one value of the mean (Zave) of impedance values during a period from the current to a predetermined time before, the product of an impedance value, a change (ΔZ) in the impedance value, and a change in the mean (ΔZave) of an impedance value is the first threshold or more. In this case, the parameter may be defined as any one of the followings.

Parameter=Zave

Parameter=$Z_t \times Z_{t-1} \times Z_{t-2} \times \ldots \times Z_{t-k}$

Parameter=ΔZ

Parameter=ΔZave

In this case, t is the current time, and k is a set time interval. In this case, a determination of a parameter value after a predetermined time interval when RF energy is applied may be determined so that handling can be performed in the ablation phase without handling a change in the initial impedance value.

A method of controlling the RF treatment apparatus when the ablation mode is applied is described below. FIG. 6 is a flowchart of the method of controlling the RF treatment apparatus in the ablation prevention mode.

The method of controlling the RF treatment apparatus when the ablation mode is applied may include a step S100 of positioning an electrode in a tissue, a step S200 of applying RF energy, a sensing step S300, a step S400 of calculating impedance, a step S500 of determining whether a parameter exceeds a first threshold, and a step S600 of cutting off the RF energy.

The step S100 of positioning an electrode in a tissue corresponds to the step of positioning the electrode close to a tissue that is a target of treatment. When the skin is treated, the electrode may be brought in contact with the skin or the electrode including a plurality of micro needles may be inserted through the skin and positioned.

The step S200 of applying RF energy corresponds to the step of applying RF energy in order to treat the tissue. In this case, the RF energy is controlled and applied depending on the state of the tissue through feedback control.

The sensing step S300 corresponds to the step of measuring a voltage, current and power applied to the electrode and a load including the tissue while the RF energy is applied. In this case, a unique impedance value may vary because the RF energy is applied to the tissue. A corresponding voltage, current and power is measured in real time.

In the step S400 of calculating impedance, impedance is calculated using the result values measured in the sensing step S300. In this case, the calculation is performed as an RMS.

The step S500 of determining whether a parameter exceeds a first threshold corresponds to the step of determining whether cut-off is necessary in order to prevent excessive energy from being transferred to the tissue. The application of the RF energy is cut off right before ablation of the tissue in order to prevent the ablation from occurring because excessive RF energy is applied within a short time.

If a temperature is measured at this time, there is a difficulty in using the temperature for feedback because time delay occurs. Accordingly, a point of time of cut-off is determined based on a parameter into which a change in the impedance ($\Delta Z$) of the tissue has been incorporated. In this case, the parameter may be determined as described above with reference to the aforementioned function of the controller.

In other words, a parameter determined based on the "phase in which a change ($\Delta Z$) in the impedance rises (impedance increment rising phase)" and "a value of the impedance during the risen phase (rising phase)". When the parameter is the first threshold or more, the RF energy may be automatically cut off. Furthermore, the parameter may be determined by incorporating the mean of impedance values during the rising phase in order to reduce an error attributable to noise.

As a result, whether a step is a step right before ablation may be determined by sensing an electrical predetermined value of the tissue over time in the state right before the ablation, and thus ablation is prevented.

The step S600 of cutting off RF energy corresponds to the step of cutting off the RF energy in order to prevent ablation if the parameter value is determined to be higher than the first threshold.

FIG. 7 is an impedance and temperature graph of a tissue when the ablation prevention mode is performed in the RF treatment apparatus. As shown, when a parameter into which a sudden rise of impedance has been incorporated reaches a first threshold when the impedance rises suddenly, RF energy is cut off so that a temperature of a tissue does not become a predetermined temperature or more. Accordingly, if a tissue has different electrical characteristics depending on a person although the tissue is located in the same portion, RF energy is cut off at a different point of time, thereby being capable of preventing ablation from occurring.

II. Coagulation Mode

Hereinafter, the coagulation mode that may be optionally applied by the controller is described in detail with reference to FIGS. 8a to 12b.

Figure 8A:
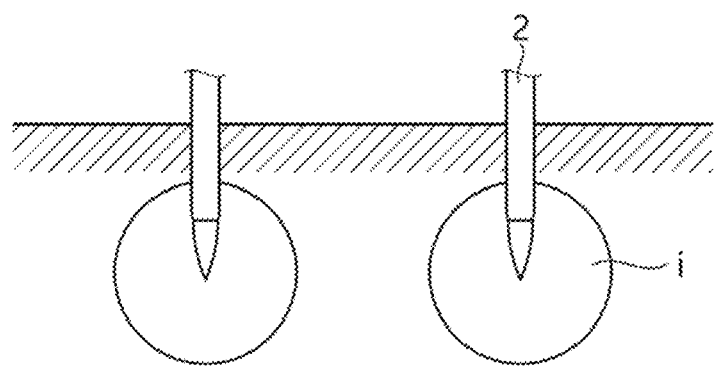
FIGS. 8a, 8b and 8c are conceptual diagrams of when coagulation within a tissue occurs.
Figure 8B:
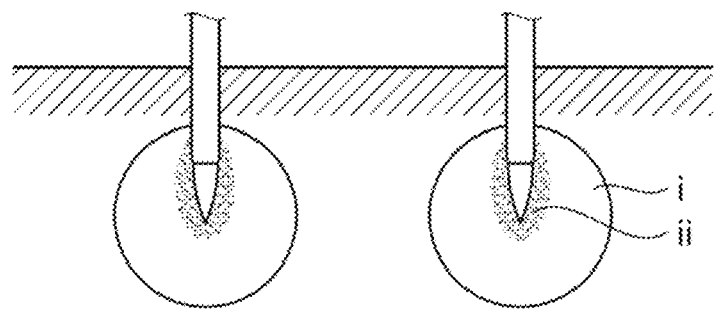

FIGS. 8a and 8b are conceptual diagrams when coagulation within a tissue occurs. As shown, a treatment lesion within a tissue when the electrode that is an invasive type and a bipolar type is used occurs around the electrode and on the path along which RF energy between the electrodes is transferred. In this case, a temperature of the tissue rises as the RF energy is applied to the tissue, so the tissue becomes a coagulation state when the temperature is about 70 to 80° C. Thereafter, if the temperature further rises, the coagulation state changes into an ablation state. It has been known that in treatment for purposes, such as wrinkle improvement and a skin elasticity increase as in the skin, ablation is not preferred and it is helpful to treat a tissue in the coagulation state.

Figure 8C:
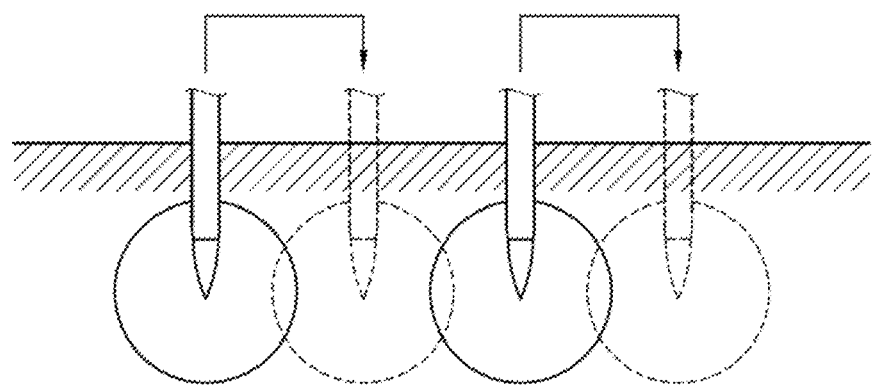

FIG. 8a shows a treatment volume (i) in which coagulation occurs when RF energy is applied. If the RF energy is suddenly applied from this point of time, ablation rapidly occurs (ii) in the treatment volume of the tissue compared to an increase of the coagulation region (i), as in FIG. 8b. In order to prevent such ablation and also increase the treatment volume in which coagulation occurs, as shown in FIG. 8c, a method of repeatedly applying RF energy to a neighboring region through insertion/reinsertion or a method using a large electrode is used. However, such a method is not appropriate for rapid treatment and a reduction of pain because a patient's pain increases due to the repetitive insertion and an insertion location needs to be precisely controlled.

Figure 9:
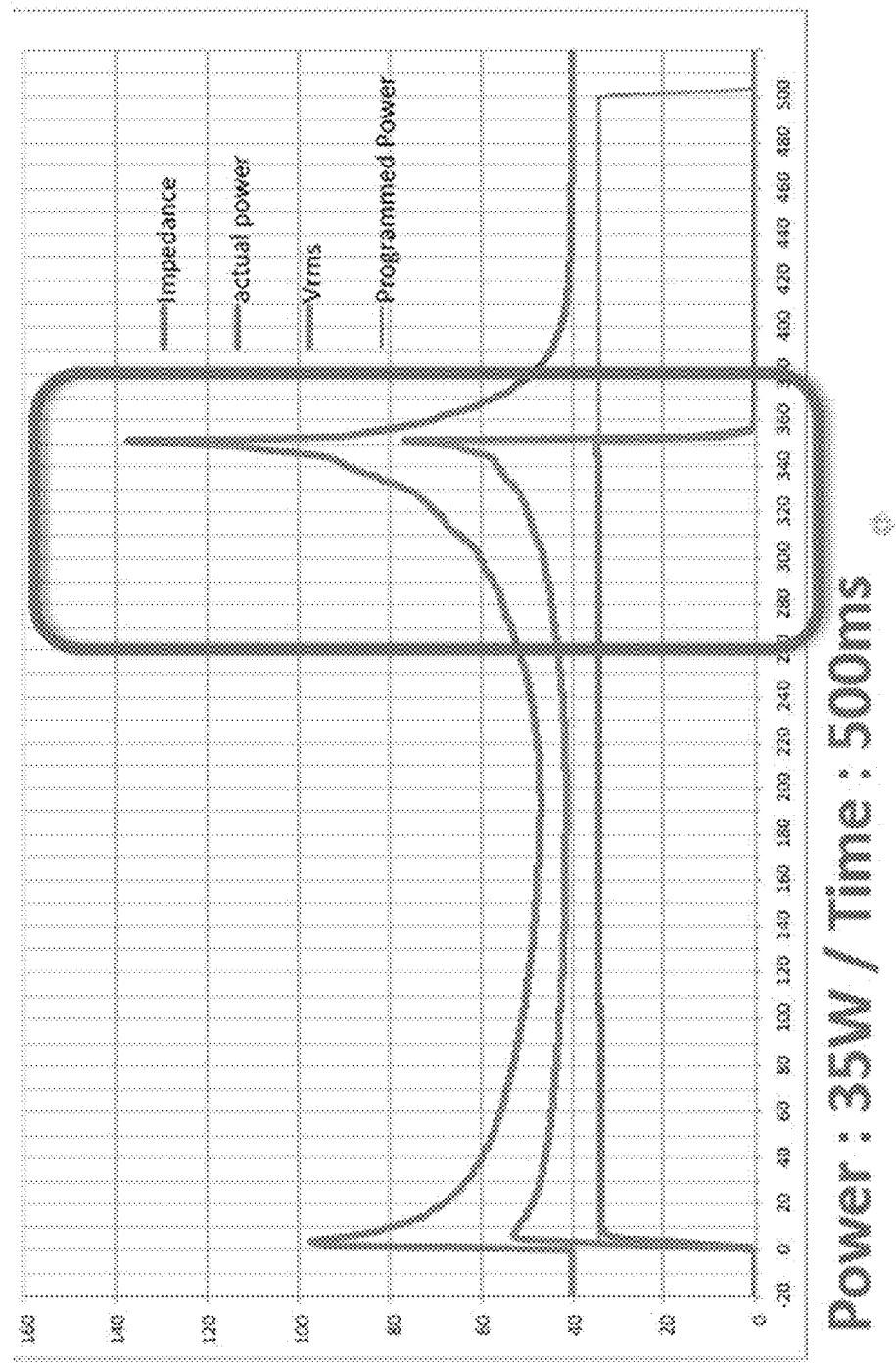
FIG. 9 is a graph showing RF energy measurement values when RF energy is applied within a tissue.

FIG. 9 is a graph showing RF energy measurement values when RF energy is applied within a tissue. As shown, when RF energy of a constant voltage is applied, RF power applied to a tissue has an initial peak value. Thereafter, the RF power tends to suddenly rise from a predetermined point of time. Meanwhile, a temperature of the target tissue gradually rises, and the temperature tends to gradually rise from a predetermined point of time. At this time, when the temperature of the tissue rises, an impedance value of the tissue also rises. As a result, RF energy is suddenly applied to the tissue. In such a case, as described above with reference to FIGS. 8a to 8c, ablation in some regions rapidly occurs compared to an increase of the treatment volume in which coagulation occurs. This occurs when the transfer of energy according to RF energy is faster than the transfer of heat toward surroundings within a target tissue.

The controller controls RF power so that a temperature of a tissue becomes constant. In this case, the temperature of the tissue may be estimated based on a change in the impedance of the tissue. If the impedance of the tissue is maintained within a constant range, the temperature can also be maintained to a predetermined level.

The controller performs control of RF energy from a point of time after a predetermined point of time, that is, from a point of time at which coagulation occurs after RF energy is applied. In this case, the sensor unit measures a voltage, current and power, and the controller calculates an impedance value based on the voltage, current and power. Such calculation may be performed as an RMS.

The controller continues to monitor a change ($\Delta Z$) in the impedance after a predetermined point of time, that is, a first application time, for example, after 50 ms (heat phase). Control may be performed when an instant impedance change exceeds a predetermined range. That is, when a change in the accumulated impedance exceeds a predetermined numerical value for a predetermined time interval up to the current time, the controller applies RF energy by increasing or decreasing RF power so that the impedance of a tissue can be maintained to a proper level. In this case, control of the RF power may be performed for a third application time.

A determination of whether the accumulated impedance exceeds the predetermined numerical value may be made by comparing a parameter value into which a change in the impedance has been incorporated with a second threshold. In this case, the comparison of the parameter includes calculating impedance from the current to a predetermined time before every sampling time cycle. For example, impedance values, such as the average of impedance, the average of impedance changes, the product of impedance, the product of the impedance mean, and the absolute value of an impedance change, may be incorporated into the parameter.

Predeterminedally, if control is performed using the mean (Zave) of impedance values, the sensor unit senses RF energy, the mean of target impedance of a tissue from the current to a predetermined time before may be calculated, and whether the second threshold is exceeded may be determined. For example, if the current time is t and the predetermined time interval is 3T, the average of impedance may be defined as "Zave=(Z(t)+Z(t−T)+Z(t−2T)+Z(t−3T))/4." Furthermore, if a treatment temperature is to be maintained, the controller may control RF energy so that the mean is maintained within a predetermined range using the mean (Zave) of the impedance for the predetermined time interval. That is, if the mean (Zave) of the impedance is lower than the second threshold, the controller can maintain the average of the impedance within the predetermined range by increasing RF power. In contrast, if the mean (Zave) of the impedance is higher than the second threshold, the controller can maintain the average of the impedance within the predetermined range by decreasing RF power.

Figure 10:
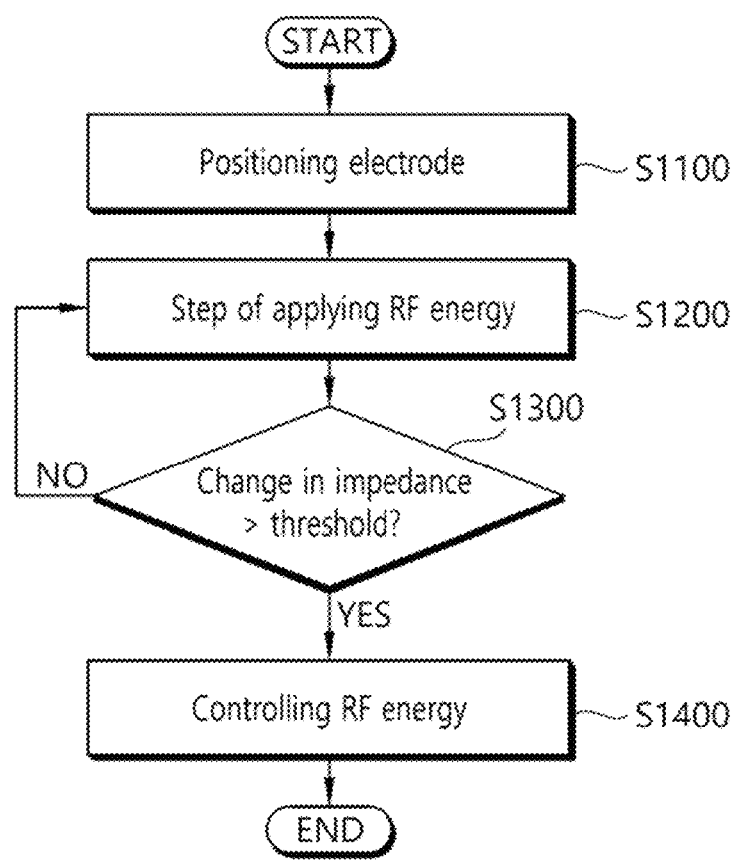
FIG. 10 is a flowchart of the coagulation mode.
Figure 11:
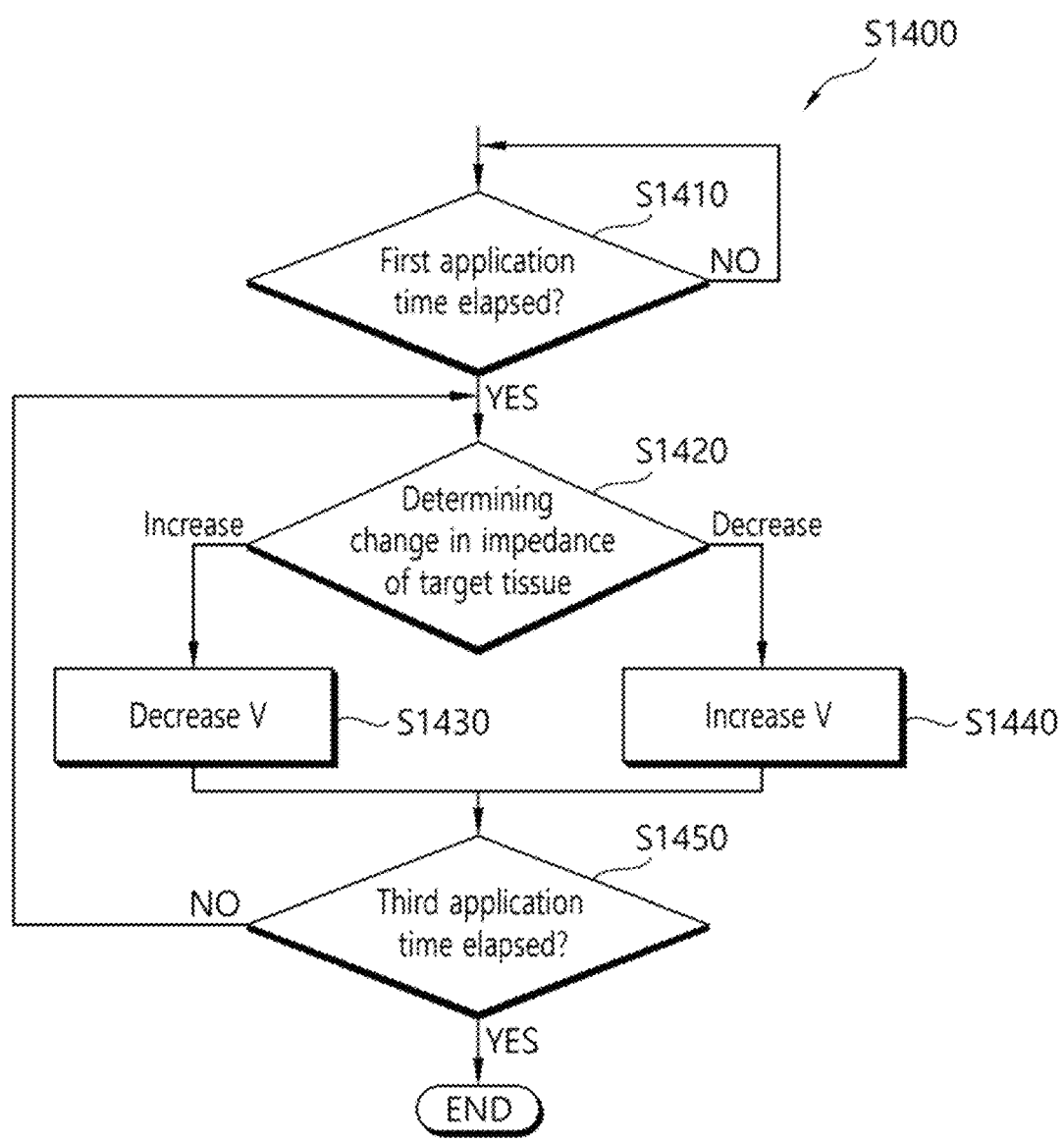
FIG. 11 is a detailed flowchart of an energy control step in FIG. 10.

FIG. 10 is a flowchart of the coagulation mode, and FIG. 11 is a detailed flowchart of the energy control step of FIG. 10.

As shown, a method of controlling the RF treatment apparatus when the coagulation mode is performed according to the present invention may include a step S1100 of positioning an electrode, a step S1200 of applying RF energy, a step S1300 of determining whether a target tissue has reached a treatment temperature, and a step S1400 of controlling the RF energy.

The step S1100 of positioning an electrode corresponds to the step of preparing treatment by positioning the electrode in a target tissue, and may be performed by bringing the electrode in contact with a surface of the target tissue, inserting the electrode into the target tissue or performing a contact and insertion at the same time.

The step S1200 of applying RF energy corresponds to the step of applying RF energy with predetermined power. In this case, the predetermined power may be a value previously set based on the size of the electrode, an array of the electrodes, the characteristics of the tissue, etc. The predetermined power may be determined based on an impedance value through the step of initially calculating an impedance value of the tissue.

The step S1300 of determining whether the target tissue has reached a treatment temperature corresponds to the step of determining whether the target tissue has reached the treatment temperature by measuring the RF power. RF power when it is applied to the tissue is monitored. If a change ($\Delta Z$) in the impedance corresponds to a range within a predetermined range, it may be determined that the target tissue has entered a stabilization step and has reached a coagulation temperature.

Furthermore, the step S1300 of determining whether the target tissue has reached the treatment temperature may be started from a first application time after the RF energy is applied. The reason for this is that in the heat phase, an impedance value of the tissue is suddenly changed and separate control of the RF power is not necessary.

The step S1400 of controlling the RF energy corresponds to the step of controlling the RF power so that a volume corresponding to the treatment temperature is maximized for a predetermined time if the target tissue has reached the treatment temperature.

Referring to FIG. 11, the step S1400 of controlling the RF energy may include a step S1410 of determining whether the first application time has elapsed, a step S1420 of determining a change in the impedance of the tissue, steps S1430 S1440 of controlling the voltage of the RF generator, and a step S1450 of determining whether a third application time has elapsed.

The step S1410 of determining whether the first application time has elapsed corresponds to the step of applying energy of preset RF power without determining whether the target tissue has reached a treatment temperature during the time corresponding to the heat phase. In this phase, impedance of the tissue may change suddenly, and thus the step is performed because separate control is not necessary.

The step S1420 of determining a change in the impedance of the tissue corresponds to the step of determining whether impedance of the tissue has changed by deriving the impedance of the tissue. The impedance of the tissue may be derived by measuring a voltage, current and power value of the RF energy applied to the electrode. In this case, an impedance value of the tissue and a change in the impedance value may be derived every moment and used for control.

The step S1430, S1440 of controlling the voltage of the RF generator corresponds to the step of controlling the RF power by controlling the voltage based on the impedance change derived in the step S1420 of determining a change in the impedance of the tissue. That is, the RF power is decreased (S1430) when the impedance value increases, and the RF power is increased (S1430) when the impedance value decreases. In the step of controlling the voltage of the RF generator, the RF power is controlled so that the transfer rate of heat toward surrounding tissues has the same level as the transfer rate of the RF energy transferred from the electrode in a local volume in which the treatment temperature has been reached. The target tissue that has reached the treatment temperature maintains the temperature, and the volume in which the target tissue has reached the treatment temperature is gradually increased. Furthermore, in control of the RF energy, the RF power may be controlled using an accumulated value of the change ($\Delta Z$) in the impedance.

In the step S1450 of determining whether the third application has elapsed, whether the step S1430, S1440 of controlling the RF power has been performed for a preset time is determined. If a preset third application time has elapsed, the RF energy is cut off and a corresponding cycle is terminated. A detailed numerical value of the third application time is omitted because the third application time may be different depending on the characteristics of a target tissue, the configuration of an electrode, etc.

Figure 12A:
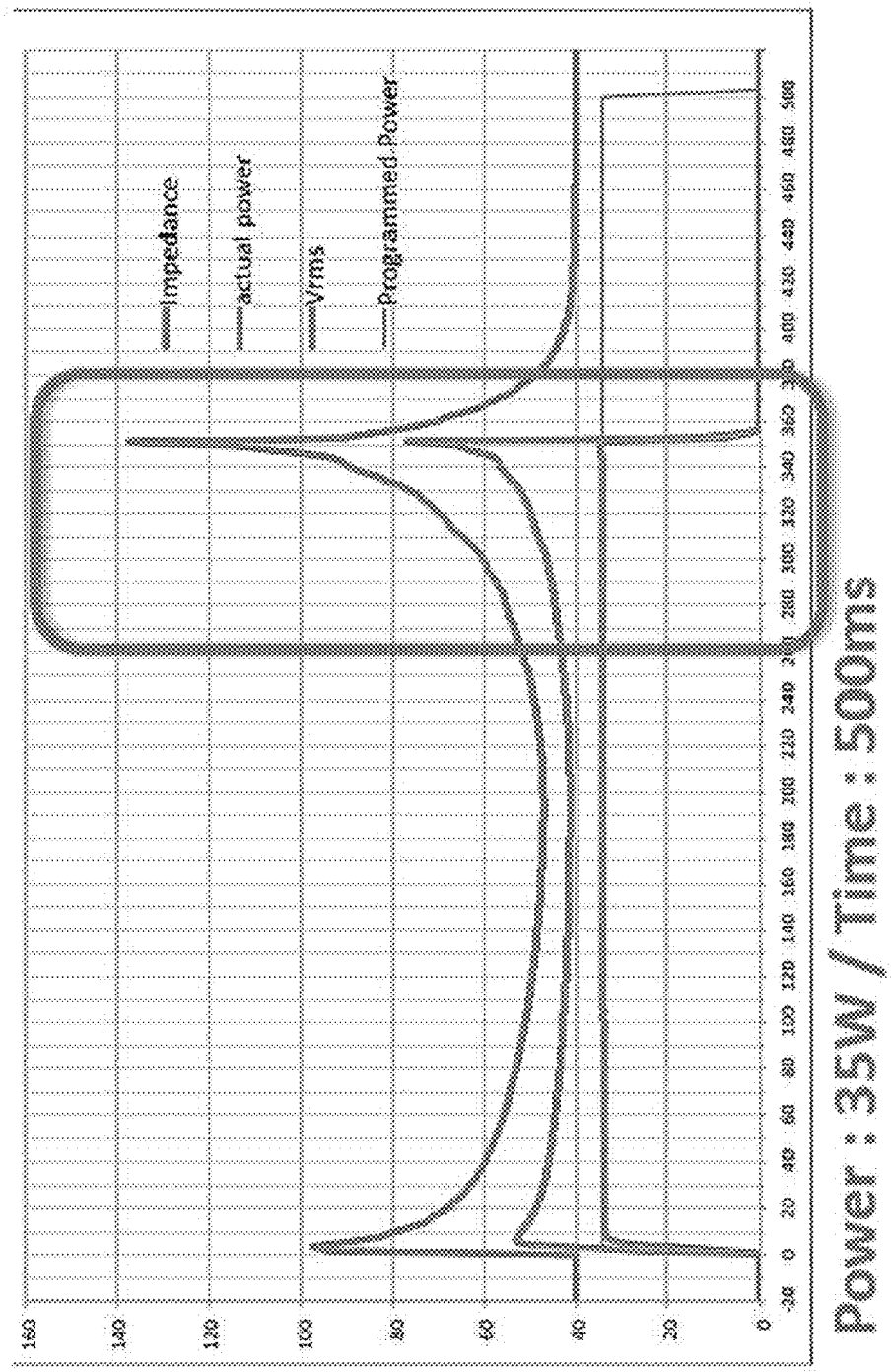
FIGS. 12a and 12b are graphs showing RF energy measurement values when the coagulation mode is performed.
Figure 12B:
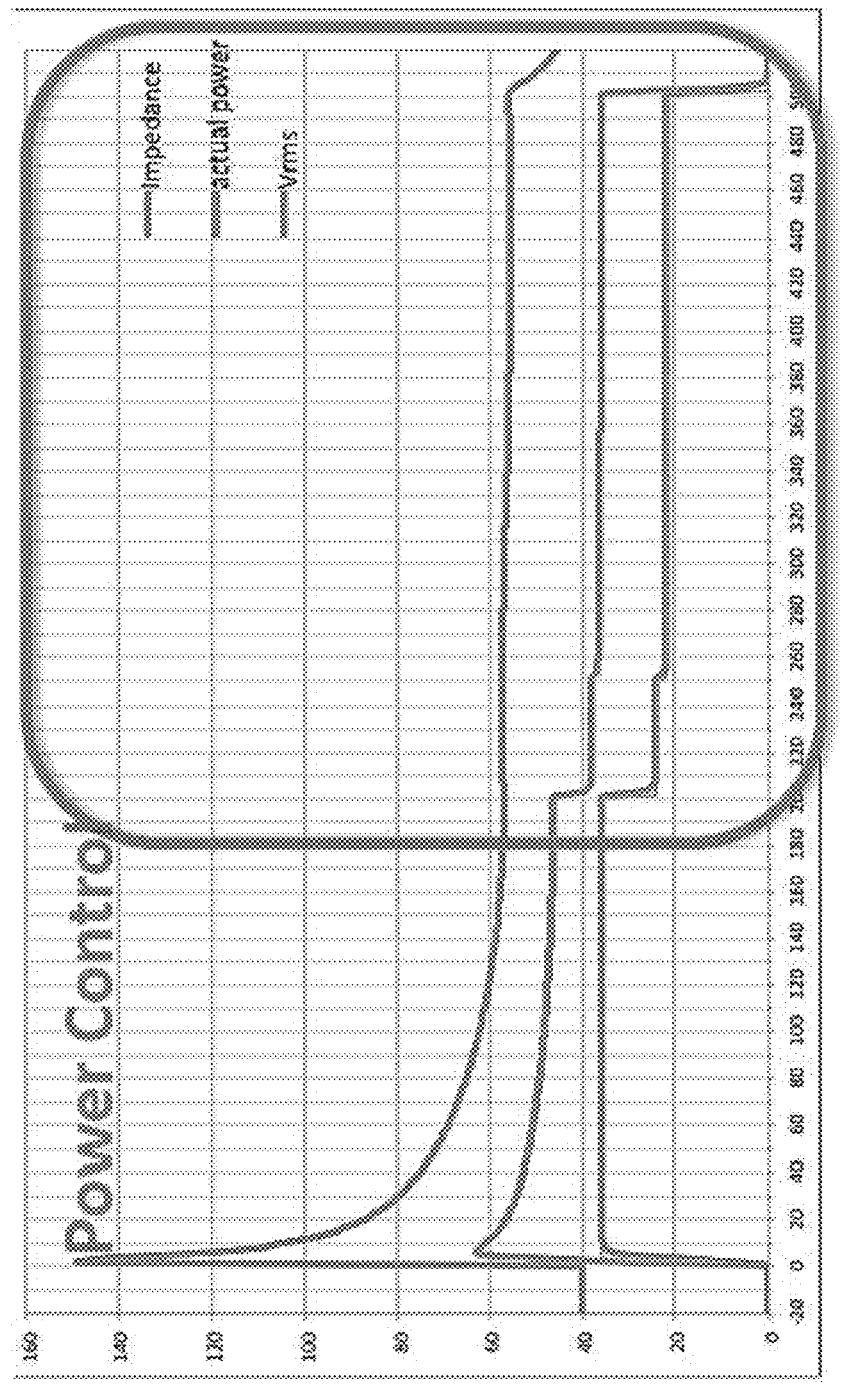

FIGS. 12a and 12b are graphs showing RF energy measurement values when the coagulation mode is performed. FIG. 12a shows a graph before the coagulation mode is performed, and FIG. 12b shows a graph after the coagulation mode is performed.

As shown, although RF power is constant after a predetermined point of time, the phase in which an impedance value of a tissue suddenly rises occurs. In this case, ablation occurs as described above. In this case, if the RF power is controlled so that the impedance maintains a constant range, the impedance can maintain a proper level as in FIG. 12(b). In this case, if control is performed based on a change ($\Delta Z$) in the impedance, an impedance change converges within a predetermined range. In such a case, if the impedance corresponds to the predetermined range, this means that a temperature of a target tissue is also maintained within the predetermined range. Accordingly, a change ($\Delta Z$) in the impedance is monitored from a point of time at which coagulation occurs. The impedance may be maintained within a predetermined numerical value by lowering the voltage of the RF power at a point of time at which the change suddenly changes.

As a result, the volume in which coagulation occurs can be expanded because a tissue can be prevented from rising to a temperature or more at which ablation occurs and the tissue can also be maintained to a treatment temperature.

Hereinafter, a detailed configuration of the RF treatment apparatus according to the present invention is described with reference to FIGS. 13 and 14.

Figure 13:
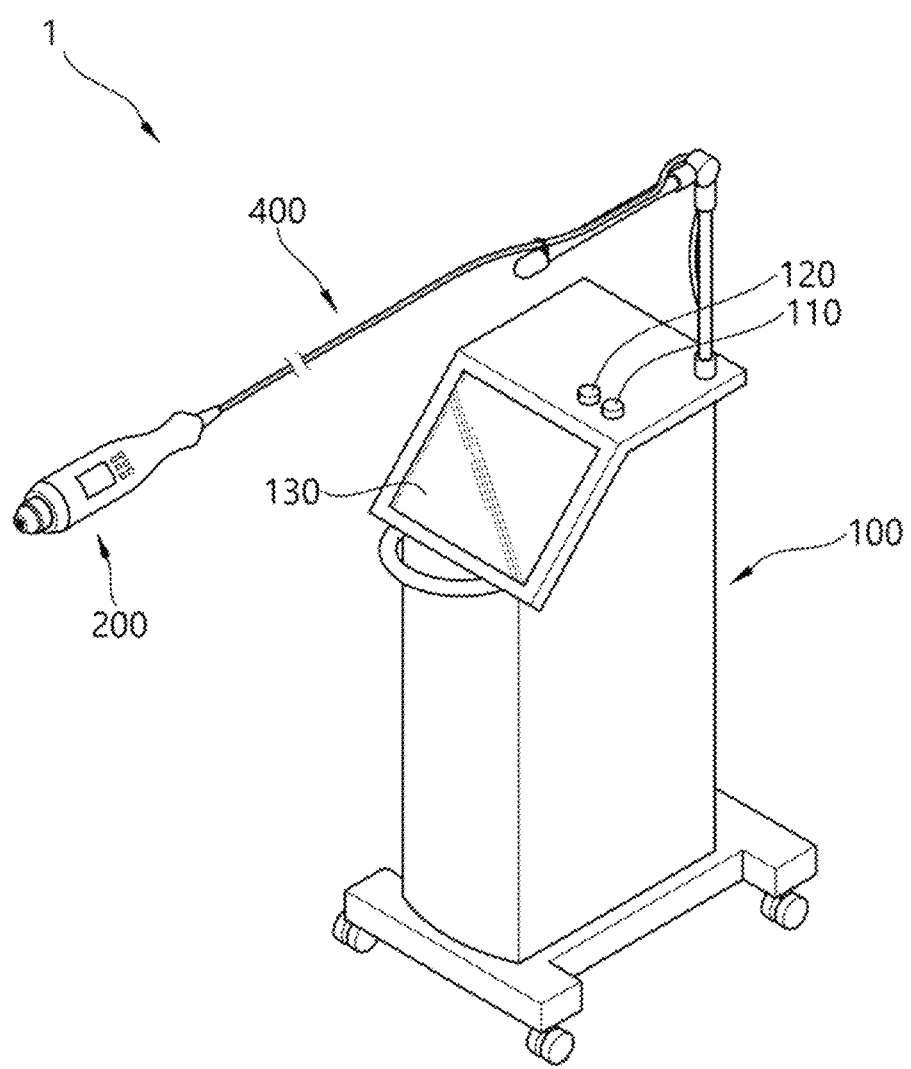
FIG. 13 is a perspective view of an RF treatment apparatus according to the present invention embodiment.
Figure 14:
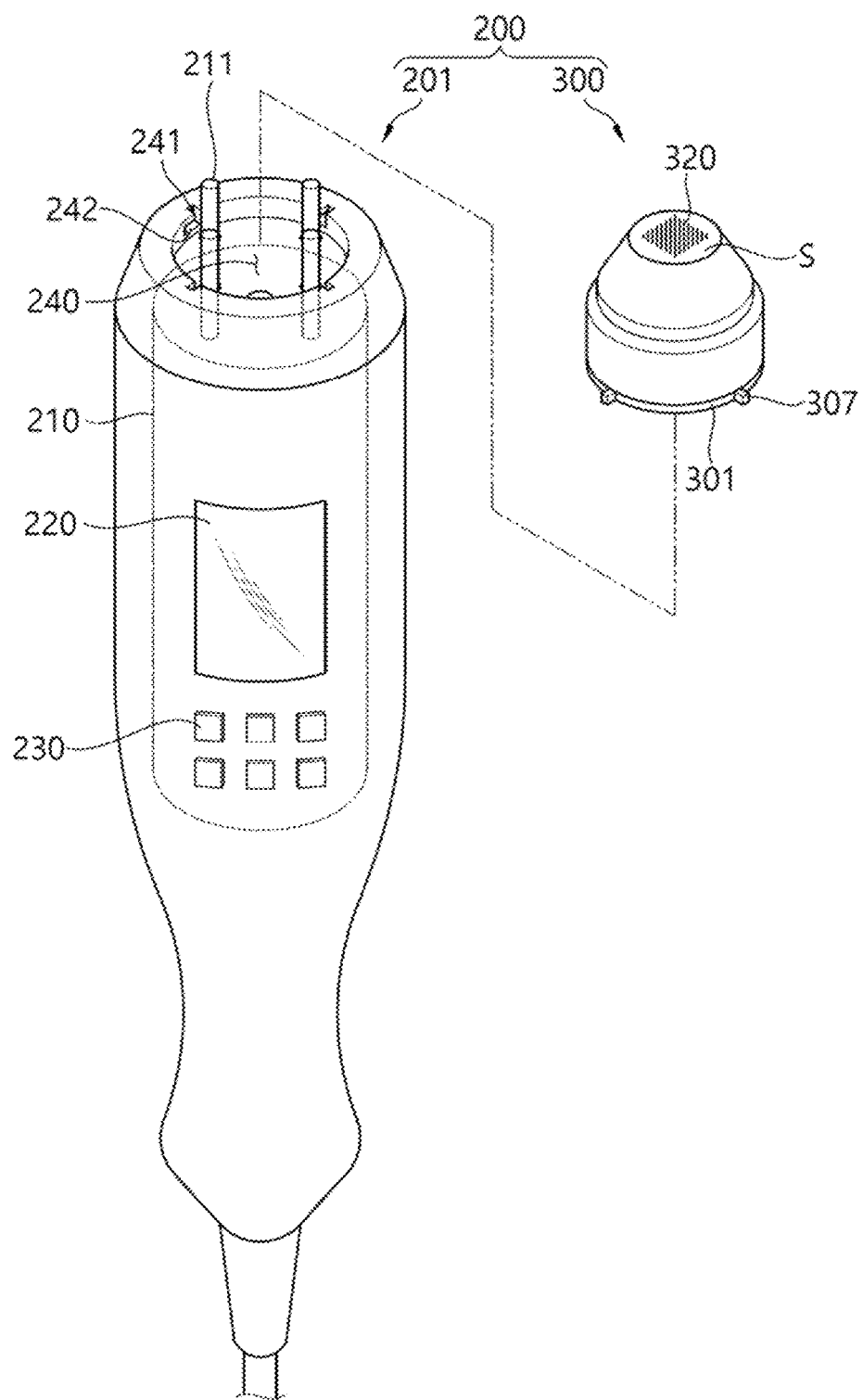
FIG. 14 is an enlarged perspective view of a handpiece of FIG. 13.

FIG. 13 is a perspective view of the RF treatment apparatus according to the present invention embodiment. FIG. 14 is an enlarged perspective view of a handpiece of FIG. 13. The RF treatment apparatus according to the present embodiment is an apparatus in which an insertion unit 10 is inserted into a skin tissue of the human body, for transferring energy into the inside of the skin tissue. The insertion unit 10 of the present embodiment includes a plurality of needles and may transfer energy to the inside of a skin tissue through the end of the needles.

The treatment apparatus according to the present embodiment is described in detail includes a main body 100, a handpiece 200 that a user can grasp and perform treatment, and a connection unit 400 connecting the main body and the handpiece.

The RF generator and the controller (not shown) may be provided within the main body 100. As described above, the controller generates a control input to control the RF generator based on a sensing value received from the sensor unit. In this case, the frequency of RF energy may be controlled depending on a patient's physical constitution, treatment purposes, a treatment portion, etc. For example, RF energy used for skin treatment may be controlled within a range of 0.1 to 10 MHz.

An on/off switch 110 of power, a frequency control lever 120 capable of controlling the frequency of RF energy generated by the RF generator, and a touch screen 130 on which a variety of types of information including operating contents of the treatment apparatus are displayed and treatment information is displayed and in which a user can input a command may be positioned on an external surface of the main body 100.

Meanwhile, the handpiece 200 is connected to the main body by the connection unit 400. The connection unit 400 may transfer RF energy, generated by the RF generator of the main body, to a plurality of needles 320 corresponding to the insertion unit 10 of the aforementioned embodiment, and may transfer power from the main body, which is necessary for various elements on the handpiece side to operate. The connection unit 400 is configured in a cable form and may use a cable including a plurality of metal lines covered with insulating coating.

A driving unit 210 and a cooling unit 40 are positioned within the housing of the handpiece 200. The driving unit 210 is configured to linearly move output terminals 211 provided at one end of the driving unit in the length direction. As the output terminals 211 move linearly, the plurality of needles 320 disposed at the end of the output terminals may appear and disappear to an external surface of a contact surface of the handpiece. Accordingly, when the driving unit 210 is driven, the plurality of needles 320 may be inserted into a patient's tissue or may be drawn out from the tissue. The driving unit 210 may be formed of a linear actuator using a solenoid or a hydraulic/pneumatic cylinder.

A handpiece manipulation unit 230 and a handpiece display unit 220 may be provided on an external surface of the handpiece 200. The handpiece manipulation unit 230 is configured to manipulate the on/off of the handpiece, control the insertion depth of the insertion unit 10 or control the amount of energy applied through the insertion unit 10. The handpiece display unit 220 may display a variety of types of information for a user during a setting mode or treatment. Accordingly, the user can easily control treatment contents during treatment through the handpiece manipulation unit 230 in the state in which the user has grasped the handpiece, and can easily check treatment contents through the handpiece display unit 220.

A tip module 300 is provided at the end of the handpiece. The tip module includes the plurality of needles 320 and may be detachably positioned in the main body 201 of the handpiece. Predeterminedally, a base 301 forms the bottom of the tip module. Outward protruded detachment protrusions 307 are formed in the outside wall of the base. A hollow through which a cooling wind from the cooling unit 40 can pass may be formed in a portion that belongs to the base 301 and that neighbors the protruded parts of the needles. Furthermore, a plurality of through holes may be formed in an outside portion that does not neighbor the protruded parts of the needles other than the protruded parts of the needles so that a cooling wind can be discharged. Guide grooves 241 guiding the detachment protrusions and anti-separation grooves 242 for preventing the detachment of the detachment protrusions 307 guided along the guide grooves 241 are formed in a recess part 240 to which the tip module is coupled on the handpiece side. Furthermore, the detachment protrusions 307 of the tip module are installed on the handpiece in such a manner that they are guided along the guide grooves 241 and coupled to the anti-separation grooves 242. Meanwhile, the tip module may be configured to cool the needles 320 by the driving of the cooling unit 40, but to seal the inside and outside of the handpiece in order to prevent an externally drained cooling wind from affecting a surface of the skin. In this case, the sealing means that a gap is formed between the handpiece and the tip module to the extent that a surface of the skin is not influenced by an externally drained cooling wind.

In this case, what the tip module is detachably positioned in the handpiece as in the present embodiment is an example. The tip module may be integrated with the handpiece.

Predeterminedly, the electrode 11 may be formed of a micro electrode 11 having a diameter of about 5 to 500 μm. The electrode 11 is made of a conductive material so that it can deliver RF energy. A portion that belongs to a surface of each electrode 11 and that excludes the front part is made of an insulating material 321 so that RF energy is not transferred to a tissue. Accordingly, part of the front part of each needle functions as the electrode 11. RF energy is applied to the tissue through the front part. Accordingly, RF energy can be selectively transferred to a portion where the end of the electrode 11 is positioned during treatment.

The front S of the tip module may form a portion that neighbors or comes into contact with the skin of a patient during treatment. The plurality of through holes 302 through the plurality of electrodes 11 appears and disappears is formed in the front.

At least one hole 303 through which the output terminals 211 can pass is provided at the bottom of the tip module. When the driving unit 210 operates, the output terminals 211 pressurize a board 13 while linearly moving along the hole 303. The back of the board 13 is seated in a support 304 within the tip module, and the front thereof is pressurized by an elastic member 330 positioned within the tip module. When the output terminals 211 moves and pressurizes the board 13, the board 13 advances while being separated from the support 304, and the plurality of electrodes 11 is inserted into a skin tissue while being protruded toward the front of the through hole 302. Furthermore, when the output terminals 211 retreat by the driving of the driving unit 210, the board 13 retreats by restoring force of the elastic member 330 and the plurality of electrodes 11 also returns to the inside of the tip module. Although not separately shown, a separate guide member for guiding the path along which the board moves may be further provided.

Although not shown in the drawing predeterminedally, the circuit of the board 13 may be configured to be electrically connected to the RF generator of the main body when the tip module is positioned in the handpiece. Alternatively, the circuit of the board may be configured to be selectively electrically connected to the RF generator when the board is pressurized by the output terminals 211 (e.g., the electrode 11 is formed at the end of the output terminal and electrically connected to the board when the electrodes is pressurized).

In addition, the present invention may provide a treatment method using RF energy. In the skin treatment method using RF energy, the electrode is positioned in a tissue, the tissue is heated by applying RF energy, the RF energy applied to the tissue is measured, impedance of the tissue to which the RF energy is applied is calculated, a parameter into which the impedance has been incorporated is compared with a threshold, whether to cut off the RF energy is determined based on the threshold, and the skin is treated.

A voltage, a potential and power are measured from the RF energy applied to the tissue. The RMS of impedance of the tissue may be calculated based on the voltage, potential and power. While the RF energy is applied, the RF energy is periodically measured according to a sampling time, impedance is calculated, and control is performed using impedance calculated from the current to a predetermined time before.

In this case, a curer may perform treatment selectively using one of the ablation prevention mode and the coagulation mode as follows. In this case, in the two modes, RF energy may be applied based on the parameter described in the method of controlling the RF treatment apparatus.

In the ablation prevention mode, if impedance suddenly rises and a parameter value is a first threshold or more, RF energy is cut off before ablation of a tissue occurs based on a symptom that the ablation may occur, thereby preventing a temperature of the tissue from rising. Thereafter, a skin treatment method using RF energy by changing the position of an electrode may be repeatedly performed.

In the coagulation mode, RF energy is controlled so that the period during which a tissue is maintained to a treatment temperature can be extended. A temperature of the tissue is estimated and RF energy is controlled based on a parameter into which an impedance value has been incorporated. Accordingly, the tissue does not rise up to a temperature at which ablation occurs and is maintained to a temperature at which coagulation occurs, so the region in which coagulation occurs is increased.

The aforementioned RF treatment apparatus, method of controlling the RF treatment apparatus, and skin treatment method using RF energy according to the present invention can be used to control power of RF energy by deriving an impedance value of a tissue without measuring the temperature and impedance of the tissue when the RF energy is applied. Accordingly, rapid and accurate control can be performed. Furthermore, there are effects in that unnecessary damage to a tissue can be prevented, stability can be improved, and the recovering of a patient can be increased by cutting off RF energy before ablation of the tissue occurs based on a parameter. Furthermore, there is an effect in that a treatment effect can be maximized because a treatment volume is expanded by maintaining a tissue to a coagulation temperature for a long time.

The invention claimed is:

1. An RF treatment apparatus, comprising:
an RF generator generating RF energy;
an electrode for applying the RF energy to a target tissue;
a sensor unit configured to sense the RF energy; and
a controller controlling output of the RF generator, receiving a sensing value from the sensor unit, calculating a rate of change of impedance of the tissue, and controlling the RF energy in a coagulation mode of treatment or in an ablation prevention mode of treatment,
wherein the controller:
in the coagulation mode of treatment, monitors a change in impedance and controls the RF energy based on the change in impedance to maintain impedance of the tissue at a specific level; and
in the ablation prevention mode of treatment, controls the RF energy based on the rate of change of impedance to prevent a sudden rise in the rate of change of impedance.

2. The RF treatment apparatus of claim 1, wherein the controller determines the target tissue has reached the treatment temperature if the rate of change of impedance of the tissue has reached within a predetermined range.

3. The RF treatment apparatus of claim 2, wherein the controller determines the target tissue has reached the treatment temperature if the change in the impedance between a current time and a predetermined time before the current time is within a predetermined range.

4. The RF treatment apparatus of claim 2, wherein when controlling the RF energy, the controller controls the RF energy by increasing RF power of the RF energy when the rate of change of impedance is less than a threshold and decreasing the RF power of the RF energy when the rate of change of impedance is the threshold or more.

5. The RF treatment apparatus of claim 2, wherein the controller:
applies the RF energy while maintaining constant RF power during a first application time from a start of treatment,
determines whether the target tissue has reached the treatment temperature after a lapse of the first application time, and
controls the RF power when the target tissue reaches the treatment temperature.

6. The RF treatment apparatus of claim 2, wherein the electrode comprising at least one of a contact type and an insertion type.

7. The RF treatment apparatus of claim 1, wherein the controller performs the control for a predetermined control time.

8. The RF treatment apparatus of claim 1, wherein the controller controls a voltage when controlling the RF energy.

9. The RF treatment apparatus of claim 1, wherein, in the coagulation mode of treatment, the controller monitors the change in impedance from a point of time at which coagulation occurs.

10. The RF treatment apparatus of claim 1, wherein the controller operates in the coagulation mode or the ablation prevention mode selectively according to a user's input.

11. The RF treatment apparatus of claim 1, wherein, in the coagulation mode of treatment, the controller applies the RF energy while maintaining constant RF power during a first time interval from a start of treatment, determines whether controlling the RF energy by increasing or decreasing the RF energy has been performed during a second time interval, and cuts off the RF energy when the second time interval has elapsed.

12. A method of controlling an RF treatment apparatus, comprising steps of:
positioning an electrode in a target tissue;
applying RF energy;
calculating a rate of change of impedance of the target tissue by sensing the RF energy and determining whether the target tissue has reached a treatment temperature based on the rate of change of impedance of the target tissue; and
controlling the RF energy in a coagulation mode of treatment or in an ablation prevention mode of treatment,
wherein, in the coagulation mode, a change in impedance is monitored and the RF energy is controlled based on the change in impedance to maintain impedance of the tissue at a specific level, and
wherein, in the ablation prevention mode, the RF energy is controlled based on the rate of change of impedance to prevent a sudden rise in the rate of change of impedance.

13. The method of claim 12, wherein the step of determining whether the target tissue has reached the treatment temperature is performed after the RF energy is applied for a first application time in the step of applying the RF energy.

14. The method of claim 13, wherein the step of controlling the RF energy comprises increasing RF power of the RF energy when the rate of change of impedance is less than a threshold.

15. The method of claim 13, wherein the step of controlling the RF energy comprises controlling power of the RF energy so that an absolute value of the rate of change of impedance is maintained within the predetermined range.

16. The method of claim 13, wherein the step of controlling the RF energy comprises decreasing RF power of the RF energy when the rate of change of impedance is a threshold or more.

17. The method of claim 14 or 15, wherein the step of controlling the RF energy is performed by controlling a voltage of the RF energy.

18. The method of claim 13, wherein the step of controlling the RF energy is performed for a preset third application time so that a volume belonging to the target tissue and corresponding to the treatment temperature is increased.

19. The method of claim 12, wherein the step of positioning the electrode in the target tissue is performed using at least one of a contact and insertion of the electrode on and into the target tissue.

20. A skin treatment method using RF energy, comprising steps of:
positioning an electrode in a tissue;
heating the tissue to a treatment temperature by applying RF energy to the electrode;
measuring the RF energy applied to the tissue;
calculating a rate of change of impedance of the tissue to which the RF energy is applied;
comparing a parameter and a predetermined range to determine whether the parameter has reached in the predetermined range, the parameter being determined based on the rate of change of impedance between a current time and a predetermined time before the current time; and
controlling power of the RF energy in a coagulation mode of treatment or in an ablation prevention mode of treatment,
wherein, in the coagulation mode, a change in impedance is monitored and the RF energy is controlled based on the change in impedance to maintain impedance of the tissue at a specific level, and
wherein, in the ablation prevention mode, the RF energy is controlled based on the rate of change of impedance to prevent a sudden rise in the rate of change of impedance.

21. The skin treatment method of claim 20, wherein the step of controlling the RF energy based on a result of the comparison comprises:
increasing the power of the RF energy when the parameter is less than a threshold, and
decreasing the power of the RF energy when the parameter is the threshold or more.

* * * * *